(12) United States Patent
Wakil et al.

(10) Patent No.: US 6,548,738 B2
(45) Date of Patent: Apr. 15, 2003

(54) ACC2-KNOCKOUT MICE AND USES THEREOF

(75) Inventors: Salih J. Wakil, Houston, TX (US); Martin M. Matzuk, Pearland, TX (US); Lutfi Abu-Elheiga, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/749,109

(22) Filed: Dec. 26, 2000

(65) Prior Publication Data

US 2002/0104111 A1 Aug. 1, 2002

(51) Int. Cl.[7] ................... A01K 67/027; C12N 5/00; C12N 5/02; C12N 15/63; C12N 15/85
(52) U.S. Cl. ..................... 800/18; 435/325; 435/455
(58) Field of Search .......................... 800/18; 435/455, 435/325

(56) References Cited

PUBLICATIONS

Moreadith et al. Gene targeting in embryonic stem cells: the new physiology and metabolism, Journal of Molecular Medicine, 1997, vol. 75, pp. 208–216.*

Moens et al. Defects in heart and lung development in compound heterozygotes for two different targeted mutations at the N–myc locus, Development, 1993, vol. 119, pp. 485–499.*

* cited by examiner

Primary Examiner—Scott D. Priebe
Assistant Examiner—Peter Paras, Jr.
(74) Attorney, Agent, or Firm—Benjamin Aaron Adler

(57) ABSTRACT

The present invention discloses transgenic mice with inactivating mutations in the endogenous gene for the acetyl-CoA carboxylase-2 isoform of acetyl-CoA carboxylase. Inactivation of acetyl-CoA carboxylase-2 results in mice exhibiting a phenotype of reduced malonyl-CoA levels in skeletal muscle and heart, unrestricted fat oxidation, and reduced fat accumulation in the liver and fat storage cells. As a result, the mice consume more food but accumulate less fat and remain leaner than wild type mice fed the same diet. These results demonstrate that inhibition of ACC2 acetyl-CoA carboxylase could be used to regulate fat oxidation and accumulation for purposes of weight control. The transgenic mice of the instant invention provide a useful animal model to identify such inhibitors and for studying the mechanisms of fat metabolism and weight control.

10 Claims, 10 Drawing Sheets

(3 of 10 Drawing Sheet(s) Filed in Color)

ACC2-KNOCKOUT MICE AND USES THEREOF

FEDERAL FUNDING LEGEND

This invention was produced in part using funds from the Federal government under N.I.H. G.M. 19091. Accordingly, the Federal government has certain rights in this invention.

BACKGROUND OF THE INVENTION

1. Field of the Invention

The present invention relates generally to the field of fat metabolism and weight control. More specifically, the present invention relates to the role of the ACC2 isoform of acetyl-CoA carboxylase in regulating fatty acid accumulation and oxidation and to transgenic mice deficient for the ACC2 isoform.

2. Description of the Related Art

Acetyl-CoA carboxylase (ACC), a biotin-containing enzyme, catalyzes the carboxylation of acetyl-CoA to form malonyl-CoA, an intermediate metabolite that plays a pivotal role in the regulation of fatty acid metabolism (1–3). It has been found that malonyl-CoA is a negative regulator of carnitine palmitoyltransferase I (CPTI, a component of the fatty-acid shuttle system (4,5) that is involved in the mitochondrial oxidation of long-chain fatty acids. This finding provides an important link between two opposed pathways-fatty-acid synthesis and fatty-acid oxidation. Thus, it is possible to interrelate fatty acid metabolism with carbohydrate metabolism through the shared intermediate acetyl-CoA, the product of pyruvate dehydrogenase. Consequently, the roles of malonyl-CoA in energy metabolism in lipogenic (liver and adipose) and non-lipogenic (heart and muscle) tissues has become the focus of many studies (4–11).

In prokaryotes, acetyl-CoA carboxylase is composed of three distinct proteins—the biotin carboxyl carrier protein, the biotin carboxylase, and the transcarboxylase (12). In eukaryotes, however, these activities are contained within a single multifunctional protein that is encoded by a single gene. In animals, including humans, there are two isoforms of acetyl-CoA carboxylase expressed in most cells, ACC1 ($M_r \sim 265,000$) and ACC2 ($M_r \sim 280,000$), which are encoded by two separate genes and display distinct tissue distribution (2–6, 13–17). Both ACC1 and ACC2 produce malonyl-CoA, which is the donor of the "$C_2$-units" for fatty acid synthesis and the regulator of the carnitine palmitoyl-CoA shuttle system that is involved in the mitochondrial oxidation of long-chain fatty acids (4, 5, 18). Hence, acetyl-CoA carboxylase links fatty acid synthesis and fatty acid oxidation and relates them with glucose utilization and energy production because acetyl-CoA, the substrate of the carboxylases, is the product of pyruvate dehydrogenase. This observation, together with the finding that ACC1 is highly expressed in lipogenic tissues such as liver and adipose and that ACC2 is predominantly expressed in heart and skeletal muscle (3,14,17,19), opened up a new vista in comparative studies of energy metabolism in lipogenic and fatty acid-oxidizing tissues.

Diet, especially a fat-free one, induces the synthesis of ACC's and increases their activities. Starvation or diabetes mellitus represses the expression of the ACC genes and decreases the activities of the enzymes. Earlier studies addressed the overall activities of the carboxylases with specific differentiation between ACC1 and Acc2. Studies on animal carboxylases showed that these enzymes are under long-term control at the transcriptional and translational levels and short-term regulation by phosphorylation/dephosphorylation of targeted Ser residues and by allosteric modifications induced by citrate of palmitoyl CoA (16, 20–25). Several kinases have been found to phosphorylate both carboxylases and to reduce their activities. In response to dietary glucose, insulin activates the carboxylases through their phosphorylation. Starvation and/or stress lead to increased glycogen and epinephrin levels that inactivate the carboxylases through phosphorylation (20–25). Experiments with rats undergoing exercises showed that their malonyl CoA and ACC activities in skeletal muscle decrease as a function of exercise intensity thereby favoring fatty acid oxidation. These changes are associated with an increase in AMP-kinase activity (25–28). The AMP-activated protein kinase (AMPK) is activated by a high level of AMP concurrent with a low level of ATP through mechanism involving allosteric regulation and phosphorylation by protein kinase (AMP kinase) in a cascade that is activated by exercise and cellular stressors that deplete ATP (7–10). Through these mechanisms, when metabolic fuel is low and ATP is needed, both ACC activities are turned off by phosphorylation, resulting in low malonyl-CoA levels that lead to increase synthesis of ATP through increased fatty acid oxidation and decreased consumption of ATP for fatty acid synthesis.

Recently, it was reported that the cDNA-derived amino acid sequences of human ACC1 and ACC2 share 80% identity and that the most significant difference between them is in the N-terminal sequence of ACC2 (3,13). The first 218 amino acids in the N-terminus of ACC2 represents a unique peptide that includes, in part, 114 of the extra 137 amino acid residues found in this isoform (14). Polyclonal antibodies raised against the unique ACC2 N-terminal peptide reacted specifically with ACC2 proteins derived from human, rat, and mouse tissues. These findings made it possible to establish the subcellular localization of ACC1 and ACC2 (14) and to later demonstrate that ACC2 is associated with the mitochondria and that the hydrophobic N-terminus of the ACC2 protein plays an important role in directing ACC2 to the mitochondria (6). ACC1, on the other hand, is localized to the cytosol.

Although these findings and the distinct tissue distribution of ACC1 and ACC2 suggest that ACC2 is involved in the regulation of fatty acid oxidation and that ACC1 is involved in fatty acid synthesis primarily in lipogenic tissues, they do not provide direct evidence that the products of the genes ACC1 and ACC2 have distinct roles.

The prior art is deficient in an understanding of the separate roles of ACC1 and ACC2 have in the fatty acid metabolic pathway. The prior art is also deficient in transgenic knockout mice generated to lack ACC2 and methods of using these transgenic mice. The present invention fulfills this long-standing need and desire in the art.

SUMMARY OF THE INVENTION

Malonyl-CoA (Ma-CoA), generated by acetyl-CoA carboxylases ACC1 and ACC2, is key metabolite in the regulation of fatty acid (FA) metabolism. $ACC1^{-/-}$ mutant mice were embryonically lethal, possibly due to lack of "$C_2$-units" for the synthesis of fatty acid needed for biomembrane synthesis. $ACC2^{-/-}$ mutant mice bred normally and had normal life spans. $ACC2^{-/-}$ mice fed normal diet did not accumulate fat in their livers as did the wild-type mice and overnight fasting resulted in 5-fold increase in ketone bodies production, indicating higher fatty acid oxidation. ACC1 and fatty acid synthase activities and malonyl-CoA contents of the livers of the ACC2$^{-/-}$ and ACC2$^{+/+}$ mice were the same, indicating that fatty acid synthesis is unperturbed yet the malonyl-CoA was not available for the inhibition of the mitochondrial fatty acid shuttle system, hence fatty acid oxidation was relatively high.

Absence of ACC2 resulted in 30- and 10-fold lower malonyl-CoA contents of muscles and heart, respectively. Fatty acid oxidation in the ACC2$^{-/-}$ soleus muscles was 30% higher than that of ACC2$^{+/+}$ mice. Addition of insulin did not affect fatty acid oxidation in the ACC2$^{-/-}$ soleus muscle, but, as expected, it did reduce fatty acid oxidation by 50% in the wild-type soleus muscle compared to that of the mutant. Isoproterenol, an analog of glucagon, had little effect on fatty acid oxidation in the muscle of the ACC2$^{-/-}$ mice but caused 50% increase in fatty acid oxidation in the soleus muscle. The higher fatty acid oxidation in the mutant mice resulted in 50% reduction of fat storage in the adipose tissue compared to that of the wild-type mice. These results are valuable to an understanding and control of fatty acid metabolism and energy homeostasis in normal, diabetic, and obese animals.

In one embodiment of the present invention, there is provided a transgenic mouse having a mutation in an endogenous gene for the ACC2 isoform of acetyl-CoA carboxylase that inactivates the protein. The ACC2 gene may be mutated by deleting one or more exons of the gene, which may be replaced by heterologous DNA sequences such as an HPRT expression cassette. In a preferred embodiment, an exon encoding a biotin-binding motif of ACC2 is replaced with an HPRT expression cassette. These mice exhibit a phenotype consisting of a reduction in malonyl-CoA levels in skeletal muscle and heart, unrestricted fat oxidation, and reduced fat accumulation in the liver and fat storage cells. The transgenic mice consume more food than wild type mice but remain lean.

In yet another embodiment of the present invention, there is provided a method of screening for an inhibitor of ACC2 isoform activity consisting of the step of administering potential inhibitors to wild type mice and screening for mice which exhibit the same phenotype of the ACC2$^{-/-}$ transgenic mice.

In yet another embodiment of the present invention, there is provided an ACC2 inhibitor identified by the above method. This inhibitor may be incorporated into a pharmaceutical composition to be administered to individuals for purposes of augmenting fatty acid oxidation and inhibiting fat accumulation to promote weight loss or maintenance.

In a further embodiment of the instant invention, a method is described for obtaining a purified preparation of ACC1 protein totally free of the ACC2 isoform by purifying ACC1 from the Acc2$^{-/-}$ transgenic mice.

In another embodiment of the instant invention, a method is provided for obtaining improved antibodies against ACC2 by generating the antibodies in the Acc2$^{-/-}$ transgenic mice.

In yet another embodiment of the instant invention, cell lines derived from the Acc2$^{-/-}$ transgenic mice are provided. Cell lines derived from muscle, heart, adipose cells, and liver cells are expected to be especially useful in bioassays and drug targeting studies.

In yet another embodiment of the present invention, a method of screening for agonists and antagonists of ACC2 is provided. This method comprises the steps of administering candidate compounds Acc2$^{-/-}$ cell lines and to cell lines derived from wild type mice followed by experiments to detect alterations in cellular activity. A compound that specifically acts on ACC2 will alter cellular activity in wild type cells but have no effects on Acc2$^{-/-}$ cells. Cellular activities that may be monitored include mRNA expression, protein expression, protein secretion, and lipid metabolism.

Other and further aspects, features, and advantages of the present invention will be apparent from the following description of the embodiments of the invention given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIGS. 5(A–B) show food intake and growth (body weight) of wild type and $ACC2^{-/-}$ mutant mice. Ten 3-week-old female mice—5 wild type and 5 $ACC2^{-/-}$ mutants—were fed a standard diet for 13 weeks.

FIGS. 6(A–C) show adipose tissue in $Acc2^{-/-}$ and wild type mice.

FIG. 7A shows the strategy used to create the targeted mutation. The exon (dark box) that contains the biotin-binding motif (Met-Lys-Met) was replaced with an HPRT expression cassette. The 3' and 5' probes used for Southern blot analysis are indicated.

FIG. 7B shows a typical pattern observed in genotyping by Southern blot analyses of genomic DNA extracted from mouse tails. The DNAs were digested with ShpI in duplicate. The blots were probed with the 5' and 3' probes indicated in FIG. 7A. The presence of only wild-type (+/+) and heterozygous (+/−) genotypes indicated that no homozygous (−/−) mice were born.

DETAILED DESCRIPTION OF THE INVENTION

Figure 1A:
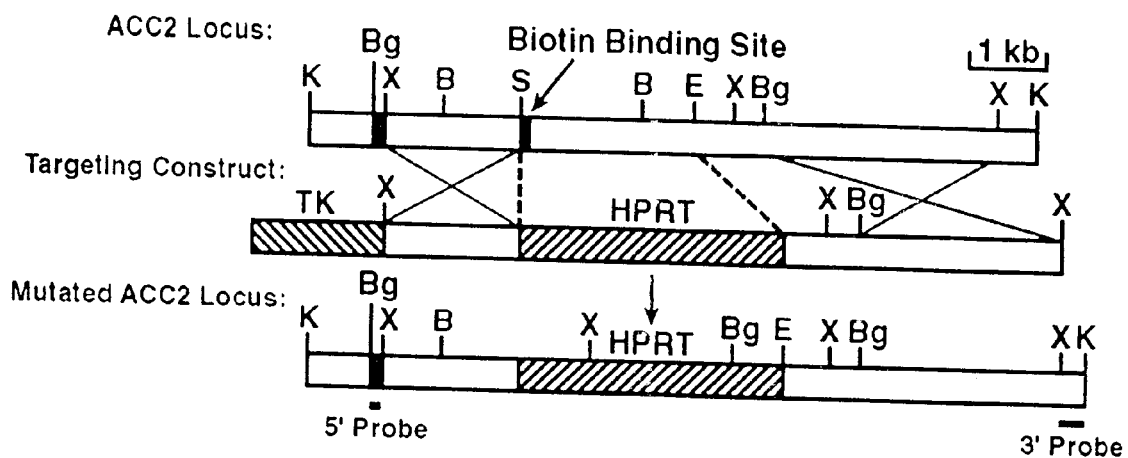
FIG. 1(A–D): shows the strategy used to create the targeted mutation. Of the two exons (dark boxes) that were identified in the mouse genomic clone, the exon that contained the biotin-binding motif (Met-Lys-Met) was replaced with an HPRT expression cassette to generate the targeting construct. The 3' and 5' probes used to identify the targeted events by Southern blot analysis are indicated.
FIG. 1B shows a Southern blot analysis of the genomic DNAs extracted from mouse tails. DNA's that were digested with BglI were probed with the 5' probe; the DNAs digested with KpnI were probed with the 3' probe. DNAs from the wild-type (+/+), heterozygous (+/−), and ACC2-null (−/−) mice gave the expected fragment sizes.
FIG. 1C shows a Northern blot of total RNA prepared from the skeletal muscles of wild-type (+/+), heterozygous (+/−), and ACC2-null (−/−) mice was probed with the $^{32}$P-labeled 362-bp cDNA fragment, which was used to screen the genomic library. The probe detected a 10-kbp RNA band in the ACC2$^{+/-}$ and ACC2$^{+/+}$ RNAs but not in the ACC2$^{-/-}$ RNA. Hybridization of the same filter (after stripping) with a mouse β-actin cDNA probe confirmed that equal amounts of RNA were loaded in the gel.
FIG. 1D shows a confirmation of the absence of ACC2 protein in the ACC2-null mice. Extracts (50 μg each) from the livers, skeletal muscles, and hearts of the mice were separated by SDS-PAGE (6%). The proteins were transferred onto a nitrocellulose filter and probed with avidin-peroxidase to detect biotin-containing proteins. The locations of the two carboxylases—the 280-kDa ACC2 and the 265-kDa ACC1—are indicated.

The present invention provides a transgenic mouse having a mutation in an endogenous ACC2 gene for the ACC2 isoform of acetyl-CoA carboxylase, which results in the lack of expression of a functional ACC2 isoform. This gene may be mutated by deleting one or more exons of the ACC2 gene, which may be replaced by heterologous DNA sequences such as an HPRT expression cassette. Preferably, an exon encoding a biotin binding motif of ACC2 is replaced with an HPRT expression cassette. The resulting mice exhibit a phenotype consisting of a reduction in malonyl-CoA levels in skeletal muscle and heart, unrestricted fat oxidation, and reduced fat accumulation in the liver and fat storage cells. The transgenic mice consume more food than wild type mice but accumulate less fat.

The present invention also demonstrates a method of screening for an inhibitor of ACC2 isoform activity consisting of administering potential inhibitors to wild type mice and screening for mice which exhibit the phenotype of the ACC2 transgenic mice.

The present invention is also directed to an ACC2 inhibitor identified by the above method. This inhibitor may be incorporated into a pharmaceutical composition to be administered to individuals for purposes of augmenting fatty acid oxidation and inhibiting fat accumulation to promote weight loss or maintenance.

The instant invention also provides a purification method for obtaining ACC1 protein that is free of the ACC2 isoform. This is accomplished by purifying ACC1 from tissue obtained from the $Acc2^{-/-}$ transgenic mice of the instant invention that lack the ACC2 isoform.

The instant invention also provides for the preparation of improved antibodies against ACC2 by generating the antibodies in the $Acc2^{-/-}$ transgenic mice. Unlike wild type mice, these mice are less immunologically tolerant of ACC2 since it is not present during the development of immunological self-tolerance. As a result, antibodies obtained from immunization of the $Acc2^{-/-}$ transgenic mice with ACC2 are more directed to unique antigenic domains of ACC2 than similar antibodies generated in wild type mice.

The instant invention is further directed to cell lines derived from the $Acc2^{-/-}$ transgenic mice. These cell lines are useful in bioassays of ACC1 and ACC2 and in drug targeting studies. Cell lines derived from the muscle, heart, adipose, and liver tissues are especially useful in these studies.

The instant invention also includes a method of screening for agonists and antagonists of ACC2. Candidate compounds are administered to both $Acc2^{-/-}$ cell lines and wild type cell lines. The cells are then monitored for alterations in cellular function such a mRNA expression, protein expression, protein secretions, and lipid metabolism. A compound that specifically acts on ACC2 will have alter cellular activity in wild type cells but will have no effect on the $Acc2^{-/-}$ cell line.

The following examples are given for the purpose of illustrating various embodiments of the invention and are not meant to limit the present invention in any fashion.

EXAMPLE 1

Generation of ACC2$^-$ Transgenic Mice

Based on the homology between the human and mouse ACC2 genes (14), two oligonucleotides from the biotin-binding region based on the cDNA sequence of human ACC2 were designed: a forward primer (5'-CTGAATGATGGGGGGCTCCTGCTCT-3'; nucleotides 2551–2575) (SEQ ID No. 1) and a reverse primer (5'-TTCAGCCGGGTGGACTTTAGCAAGG-3'; nucleotides 2890–2913) (SEQ ID No. 2). These primers were used to amplify cDNA from a Quick-Clone mouse heart cDNA pool (Clontech) template.

The cDNA fragment obtained was sequenced and used to screen a 129/SvEv mouse genomic library to isolate a 16-kbp λ genomic clone. By digesting the 16-kbp λ genomic clone with different restriction enzymes, a restriction map was established and a gene targeting vector constructed that contained positive-negative selection markers and lacked the exon that contains the biotin-binding motif Met-Lys-Met (FIG. 1A). This vector was used to generate murine 129SvEv ES cells with one mutant copy of ACC2 gene (the mutant allele was termed Acc2$^{tm1\ LAE}$).

Figure 1B:
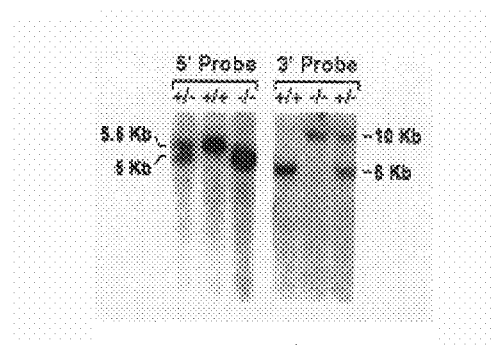

Two independent ES-cell clones were injected into mouse blastocysts, which were then implanted into the uterine horns of pseudopregnant females. Among the pups produced, eight high-level chimeras were identified and crossbred with C57BL/6J females. Each female gave birth to several agouti pups, indicating germ-line transmission of the ES-cell genome. Southern blot analysis of genomic DNA confirmed the presence of both the endogenous and the disrupted alleles in the F1 heterozygotes. The heterozygous mice were intercrossed, and their offspring were genotyped. Southern blot analyses showed that the DNA hybridized with the 5' and 3' probes shown in FIG. 1A and gave the signals expected from the wild-type (+/+), heterozygous (+/−), and homozygous-null (−/−) animals (FIG. 1B). After genotyping more than 300 mouse tails, it was determined that 24% of the progeny were ACC2$^{-/-}$, 22% were ACC2$^{+/+}$, and 54% were ACC2$^{+/-}$; these results are consistent with Mendelian inheritance. The ACC2$^{-/-}$ mutants were viable, bred normally, and appeared to have a normal life span.

EXAMPLE 2

ACC2 Expression in ACC2$^-$ Transgenic Mice

Figure 1C:
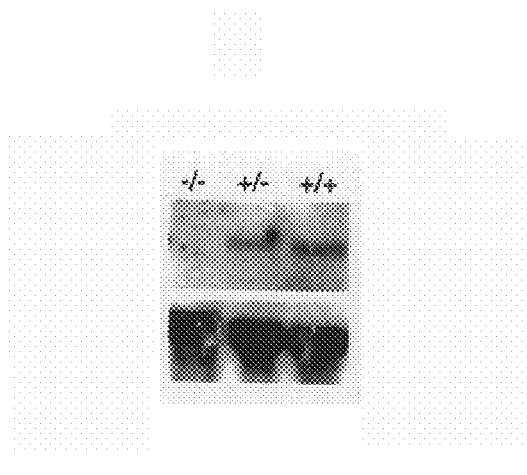
Figure 1D:
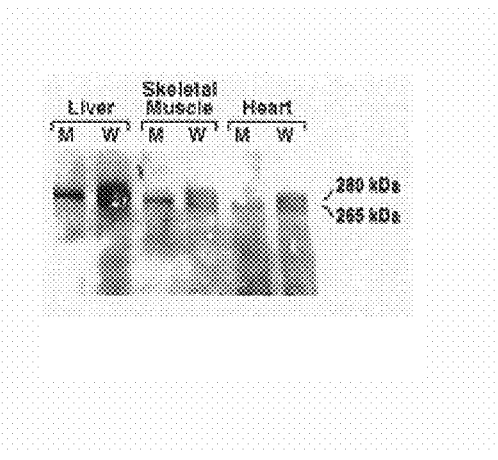

Northern blot analyses of total RNA of skeletal muscle tissues resected from the wild-type, heterozygous, and homozygous-null animals showed no detectable ACC2 mRNA in the homozygous-null animals and, as expected, the level of ACC2 mRNA in the heterozygous animals was half of that in the wild-type (FIG. 1C). Western blot analyses of heart, skeletal muscle, and liver tissues from the ACC2$^{-/-}$ mutant mice using avidin peroxidase to detect biotin-containing proteins showed no expression of ACC2 protein (FIG. 1D). The levels of ACC2 protein (280 kDa) were higher than those of ACC1 protein (265 kDa) in the heart and skeletal muscle tissues of the wild-type mice, whereas the ACC1 protein was more predominant in their liver tissues. The absence of ACC2 protein in the ACC2$^{-/-}$ mutant mice was further confirmed by confocal immunofluorescence microscopic analysis using affinity-purified anti-ACC2-specific antibodies (6). Whereas the hearts, skeletal muscles, and livers of the wild-type mice had abundant expression of ACC2 antigen, there was no expression of this protein in the ACC2$^{-/-}$ mutant mice (data not shown). Thus, by all measurements, the Acc2 mutant allele is a null allele.

EXAMPLE 3

Malonyl-CoA Levels in ACC2$^-$ Transgenic Mice

Figure 2:
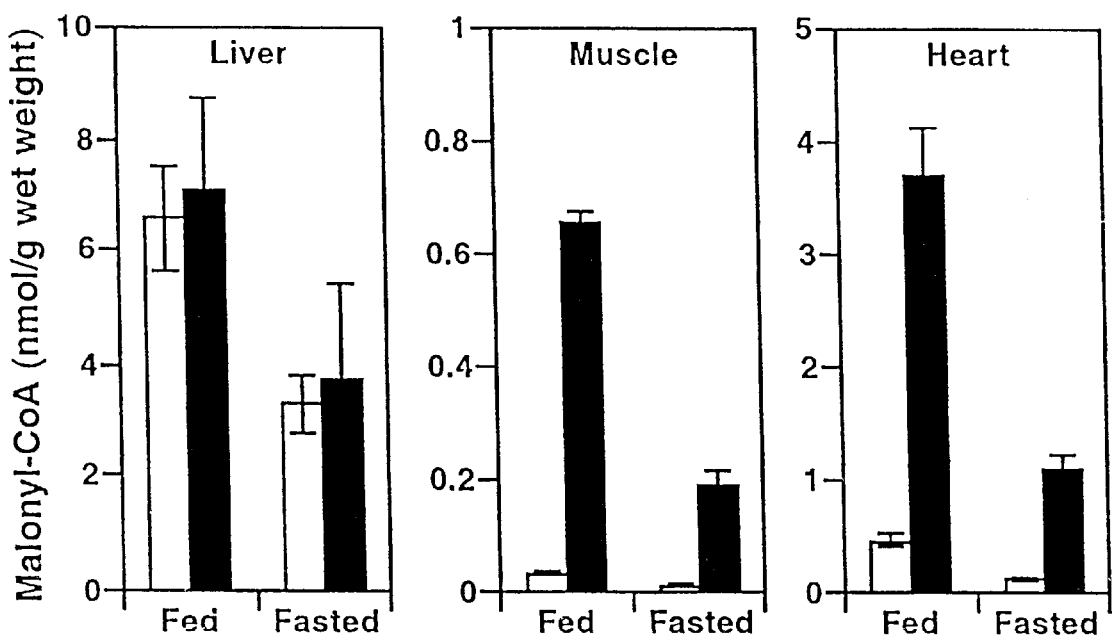
FIG. 2 shows the levels of malonyl-CoA in the tissues of wild-type (+/+) and ACC2 mutant (−/−) mice. The levels of malonyl-CoA in the mouse tissue extracts were determined by the incorporation of [$^3$H]acetyl-CoA into palmitate in the presence of NADPH and highly purified chicken fatty acid synthase (4,29). The [$^3$H]palmitic acid synthesized was extracted with petroleum ether and the radioactivity was measured. The mice were either fed normal chow or were fasted for 48 hours before they were sacrificed.

Since the levels of malonyl-CoA in animal tissues are attributed to the activities of both ACC1 and ACC2, the consequences of the absence of ACC2 on the malonyl-CoA levels in these tissues and whether ACC1 can compensate and, consequently, raise the levels of malonyl-CoA in these tissues was determined. In comparing the liver tissues of the wild-type and ACC2$^{-/-}$ mutant mice, there were no significant differences in the malonyl-CoA levels and overall ACC activities, suggesting that almost all of the malonyl-CoA in the liver is contributed by ACC1 (FIG. 2).

On the other hand, in comparing the skeletal muscle and heart tissues of the same two groups of mice, the levels of malonyl-CoA to be about 30- and 10-fold lower, respectively, in these tissues of the ACC2$^{-/-}$ mutant mice than in those of the wild-type mice. This suggests that ACC2 is the main contributor of malonyl-CoA in skeletal muscle and heart (FIG. 2). During fasting, the levels of malonyl-CoA dropped comparably in the liver tissues of both the wild-type and the ACC2$^{-/-}$ mutant mice, suggesting that ACC1 is affected by dietary conditions (FIG. 2). The levels of malonyl-CoA in the heart and muscle tissues of the fasted ACC2$^{-/-}$ mutant mice were very low, suggesting that ACC1 in these tissues is also affected by diet (FIG. 2). Since malonyl-CoA in the muscle is generated primarily by ACC2 (3), starving the wild-type mice reduced its levels by 70% from that in the muscles of the well-fed mice, suggesting that the ACC2 activity in these mice might be regulated by diet. ACC2 activity may be significantly reduced by a decrease in the amount of ACC2 expressed or by down-regulation of its activity or by both.

EXAMPLE 4

Fatty Acid Accumulation in ACC2$^-$ Transgenic Mice

Figure 3A:
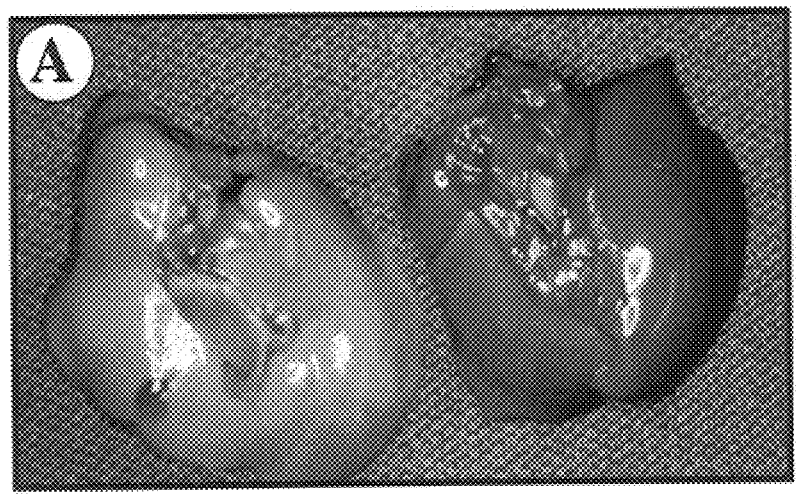
FIG. 3A shows livers of wild-type (left) and Acc2$^{-/-}$ mutant mice (right after 24 hours of starvation. Frozen sections of wild type and mutant livers were stained with Oil Red-O to detect lipid droplets and counter-stained with Mayer's hematoxylin. The liver sections of wild type mice (FIG. 3B) show an abundance of red-stained lipid droplets compared to the dramatic decrease in red-stained droplets in the $Acc2^{-/-}$ mutant liver (FIG. 3C). Frozen sections of the same livers were made from the same livers and stained for glycogen by the periodic acid-Schiff method and counter-stained with hematoxylin. The wild type livers (FIG. 3D) contain glycogen (pink-stained) and unstained lipid vacuoles, whereas the mutant livers (FIG. 3E) have little or no glycogen and few lipid vacuoles.
Figure 3B:
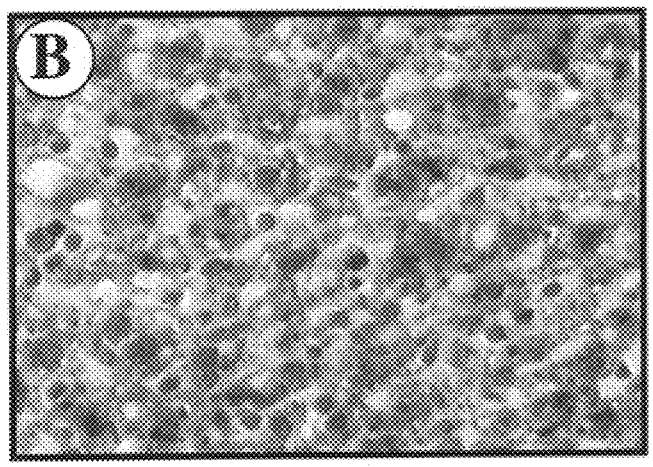
FIGS. 3(A–E) show histological analyses of livers of 32 week old male mice fed a standard diet.
Figure 3C:
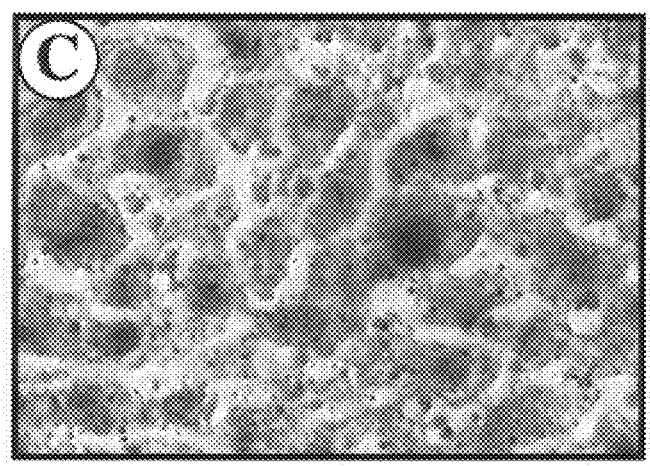

Since the ACC reaction is the rate-determining step in fatty acid synthesis (2) and because the levels of malonyl-CoA in the livers of the wild-type and ACC2$^{-/-}$ mice were nearly the same, fatty acid synthesis, which is determined by the level of malonyl-CoA, would be the same in both mouse groups. Indeed, the synthesis of palmitate measured by the incorporation of $^{14}$C-acetyl-CoA was the same for the livers of both the wild type and mutant mice (data not shown). However, the fat content of the two livers, specifically the triglyceride content, was different. The livers of the wild-type mice stored more fat, as evidence by their much lighter color compared to the livers of mutant mice of equal age and sex that had been fed the same diet (FIG. 3A). To confirm this supposition, liver tissues were stained with Oil Red-O to detect lipids and quantitate their total lipid and triglyceride content. The stained liver sections from adult wild-type mice contained abundant lipid droplets (FIG. 3B), which are primarily triglycerides, whereas those from the ACC2$^{-/-}$ mutant mice contained significantly fewer lipid droplets (FIG. 3C).

EXAMPLE 5

Analysis of Total Lipids in the Liver of ACC2$^-$ Transgenic Mice

Extracting the total lipids and analyzing them by thin-layer chromatography further confirmed the significant reduction in the accumulation of triglyceride in the liver. The total lipids of the livers of the ACC2$^{-/-}$ mutant mice were 20% lower than those in the livers of the wild-type mice, and the triglyceride content of these lipids was 80% to 90% lower in the livers of the ACC2$^{-/-}$ mutant mice than in those of the wild-type.

The ACC and fatty acid synthase (FAS) activities in liver extracts of wild-type and ACC2$^{-/-}$ mutants were very similar (data not shown). Thus, the difference in the liver lipid content must have occurred because of uncontrolled mitochondrial fatty acid oxidation in the livers of the ACC2$^{-/-}$ mutant mice, rather than resulting from a reduction in fatty acid synthesis. Also, since malonyl CoA is a negative regulator of the mitochondrial carnitine palmitoyl-CoA shuttle system (5), it absence in the livers of the Acc2$^{-/-}$ mutant mice leads to increased fatty acid translocation across the mitochondrial membrane, causing the fatty acids to be available for as substrates for the β-oxidation that primarily occurs in the mitochondria. Altogether, these results provide the strongest evidence thus far that malonyl-CoA, which is synthesized by ACC2, does affect the accumulation of lipids in the liver by controlling fatty acid oxidation. Since ACC1-generated malonyl-CoA, abundant in the livers of both groups of mice, apparently does not reduce the β-oxidation of fatty acids, it can be concluded that the malonyl-CoA produced by ACC1 and ACC2 exist in two distinct compartments of the cell—the cytosol and the mitochondria, respectively and carry out distinct function in these compartments.

EXAMPLE 6

Analysis of Glycogen in the Liver of ACC2$^-$ Transgenic Mice

Glycogen, the storage form of glucose in the liver and muscles, plays an important role in energy homeostasis in animals including humans. Its synthesis and degradation is closely related to glucose metabolism. The enzymes involved in glycogen metabolism are highly regulated by hormones such as insulin, glucagon, and epinephrine. To test whether the Acc2$^-$ null mutation might affect the level of liver glycogen, livers resected from wild-type and Acc2$^{-/-}$ mutant mice were fixed in formaldehyde and stained for glycogen by using the periodic acid-Schiff method.

Figure 3D:
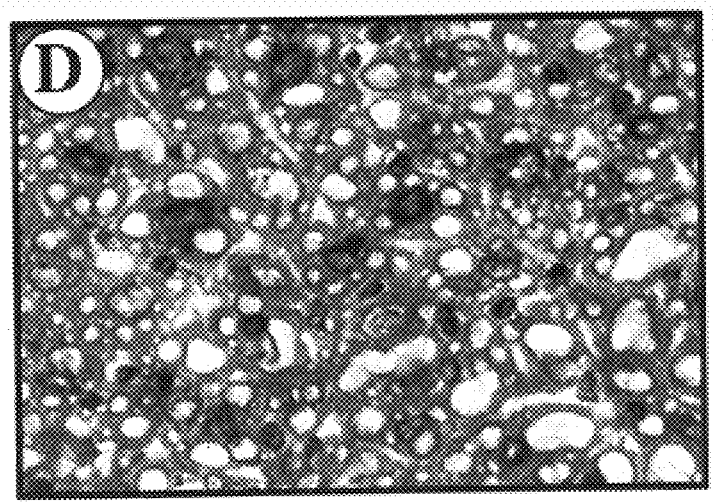
Figure 3E:
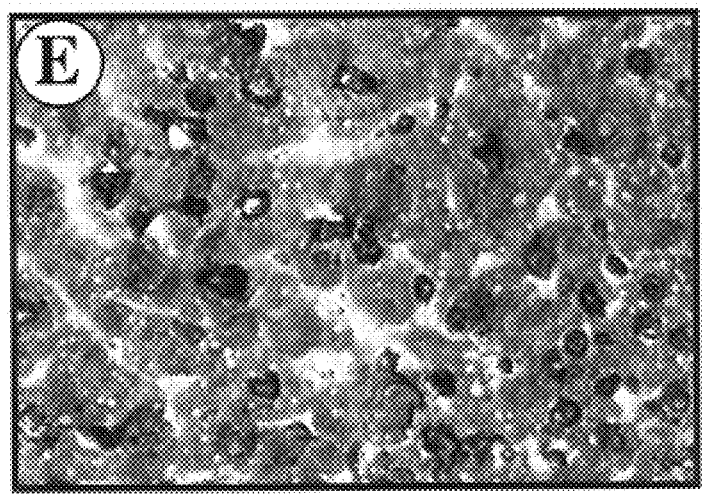

In the nourished state, the livers of the wild-type mice contained abundant amounts of glycogen (410±10 µmol/g wet tissue). The synthesis and accumulation of glycogen in the livers of the wild-type mice was expected when fed a normal diet since high dietary carbohydrate leads to active glycolysis, generation of ample energy, and the substrates required for the synthesis of glycogen and fatty acids. Acc2 is highly active under these metabolic conditions, and the malonyl-CoA that is generated inhibits carnitine palmitoyl transferase I, which then leads to decreased fatty acid oxidation. Nevertheless, the glycogen content of the livers of the Acc2$^{-/-}$ mutant mice was 20% less than that in the livers of the wild-type mice. The reason for this difference has not been established, but it is hypothesized that more glucose is utilized in the synthesis of fatty acids and their subsequent oxidation in the Acc2$^{-/-}$ mutant mouse livers. In the 24 hour fasted wild-type mouse liver shown in FIG. 3, glycogen is clearly present (FIG. 3D), while in that of the Acc2$^{-/-}$ mutant, there is little or no glycogen (FIG. 3E). In the 48 hour-fasted state, as expected, there was a significant drop in the glycogen levels in the livers of the wild-type mice to 12.6±1 µmol/g wet tissue, and a further 12-fold drop was observed in the liver glycogen content of the Acc2$^{-/-}$ mutant over that of the wild-type mouse.

EXAMPLE 7

Fatty Acid Oxidation in ACC2$^-$ Transgenic Mice

Figure 4:
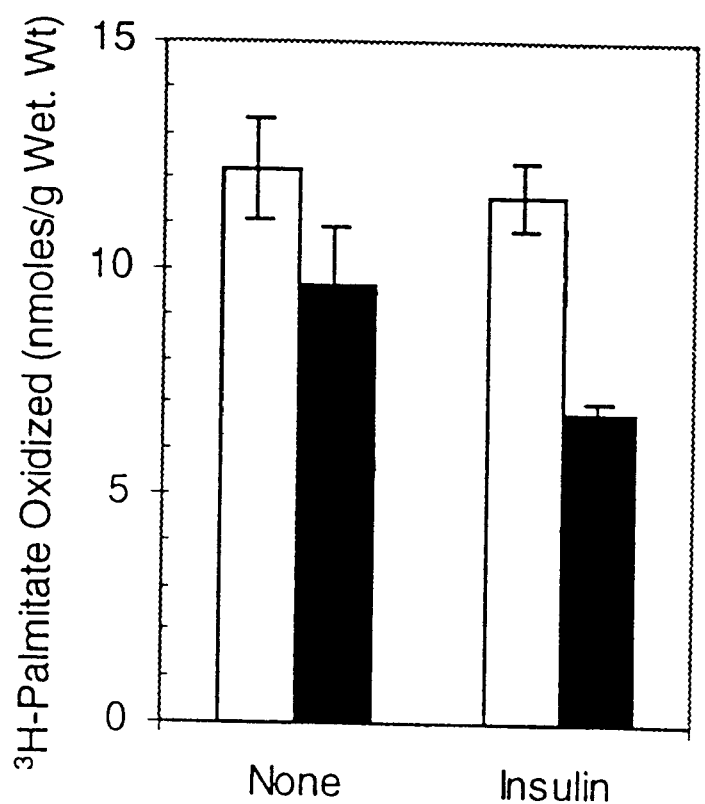
FIG. 4 shows a summary of an experiment in which mice were sacrificed by cervical dislocation, and the soleus muscles—two from each hind limb—were resected from each mouse and were immersed in 1.5 ml of Krebs-Henseleit buffer (pH 7.4) containing 4% fatty acid-free bovine serum albumin, 10 mM glucose, and 0.3 mM [9,10(n)-$^3$H]palmitate (3 mCi/vial) [Ibrahimi, 1999 #423]. Where indicated, insulin (10 nM) or isoproterenol (3 mM) was added, and the vials were incubated at 37° C. under a humidified $O_2/CO_2$ (95/5%) atmosphere for 30 min. At the end of incubation period, the $[^3H]_2O$ was separated from the labeled substrate and counted.

To provide further evidence for the role of ACC2-synthesized malonyl-CoA as the regulator of fatty acid oxidation, fatty acid oxidation was investigated in the mouse soleus muscle, a type II muscle tissue responsive to hormonal regulation (13-1510,11,28,29). As shown in FIG. 4, the oxidation of [$^3$H]palmitate was 30% higher in the isolated soleus muscles of ACC2$^{-/-}$ mutant mice than in those of the ACC2$^{+/+}$ mice. Insulin is known to activate both ACC1 and ACC2 and, thereby, to induce fatty acid synthesis and to reduce fatty acid oxidation, respectively. Adding insulin to soleus muscles resected from wild-type and from ACC2$^{-/-}$ mutant mice did not affect fatty acid oxidation in the ACC2$^{-/-}$ mutant muscle cells (FIG. 4) but did reduce palmitate oxidation by about 45% in the wild-type muscle cells (FIG. 4). Based on these results, it can be concluded that the insulin-mediated inhibition of β-oxidation occurs through the activation of ACC2, probably by (16,18,20, 22–24)(7–10, 19–24).

The role of ACC2 in the regulation of mitochondrial oxidation of fatty acids was further confirmed by using isoproterenol, an analog of glucagon, which produces effects opposite of those of insulin. Adding isoproterenol to wild-type soleus muscle increased palmitate oxidation by 50% (FIG. 4), raising it to nearly the same level as that found in the mutant muscle cells. It is noteworthy that isoproterenol also further increased fatty acid oxidation in the mutant soleus muscle cells (FIG. 4). This additional increase may be due to factors independent of malonyl-CoA (20). Altogether, these results confirm for the first time that mitochondria-associated ACC2, and not cytosolic ACC1, is responsible for the insulin-mediated activation and isoproterenol (glucagon)-mediated inactivation that results, respectively, in decreased and increased fatty acid oxidation. Since the mitochondrial CPTI activities of the soleus muscles from both groups of mice were very similar (data not shown), the observed effects of these hormones are solely due to their effect on ACC2.

EXAMPLE 8

Analysis of Blood Glucose and Lipids in ACC2$^-$ Transgenic Mice

To determine the consequence of the ACC2-null mutation on blood glucose and lipids, the serum levels of triglycerides, cholesterol, and glucose were analyzed in wild-type and ACC2$^{-/-}$ mutant mice fed a standard diet. The blood cholesterol levels were similar in both groups of mice (92.8±3.1 and 95.1±7.4 mg per deciliter). The blood glucose levels were 20% lower in mutant mice (176.6±6.5 vs. 136.2±54 mg per deciliter), whereas the triglyceride levels were 30% higher in the mutant mice fed a standard diet (35.1±2.5 vs. 45.2±59 mg/deciliter). The levels of the blood ketone bodies (γ-hydroxybutyrate) of both wild type and mutants maintained on standard diet were very low—nearly undetectable. However, fasting overnight (10–12 hr) increased the blood γ-hydroxybutyrate concentration of the ACC2$^{-/-}$ mice 5-fold over that of the wild type (2.5±0.6 mM in mutant blood vs. 0.7±0.5 of the wild type), indicating that a significantly higher degree of fatty acid oxidation had taken place in the mutant mice over that of the wild type.

EXAMPLE 9

Feeding Experiments with ACC2$^-$ Transgenic Mice

Figure 5A:
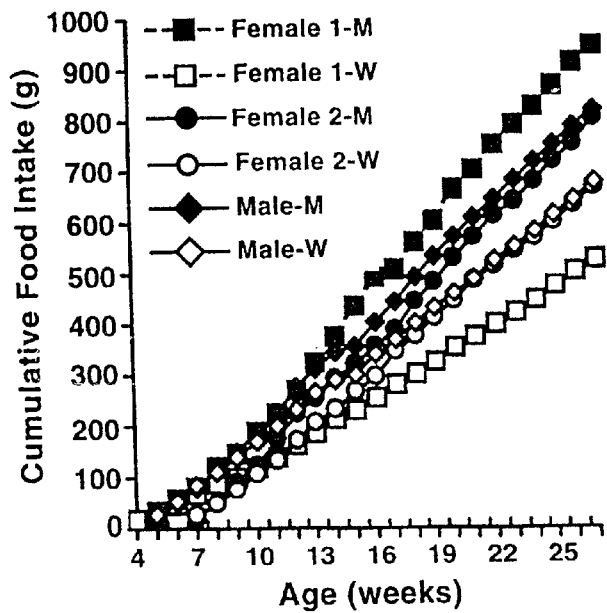
FIG. 5A: The weight of each mouse within each group was measured weekly; the average and variance of the weights are shown.
Figure 5B:
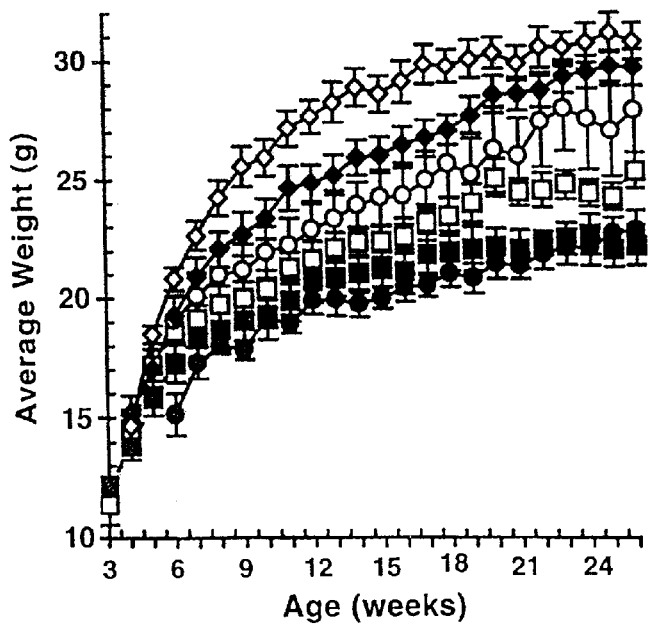
FIG. 5B: Food intake was measured every week and was expressed as cumulative food intake per mouse over the 13-week period.

Based on the results presented above, it appears that the mitochondrial β-oxidation of fatty acids occurred in the ACC2$^{-/-}$ mutant mice in an unregulated yet sustained manner. To understand the role of this type of fatty acid β-oxidation and its effect on food consumption and weight gain, feeding experiments involving three groups of mice were carried out, each consisting of one subgroup of 3- to 4-week-old female mice (5 wild-type and 5 ACC2$^{-/-}$ mutant mice) and a second subgroup of 3- to 4-week-old male mice (5 wild-type and 5 ACC2$^{-/-}$ mutant mice), that were fed a weighed standard diet ad liberatum (FIG. 5 represents a plot of one of the groups). Food consumption (no spillage was noted) for each group was measured every week for 15 to 20 weeks, and the weight of each mouse was recorded weekly.

Figure 6A:
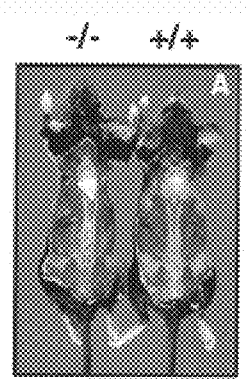
FIG. 6A shows a dorsal view of male littermates, aged 32 weeks, fed with a standard diet. Reduced white fat is observed under the skin of the $Acc2^{-/-}$ mouse (−/−, 33.6 g weight) compared with the wild type mouse (+/+, 34.2 g weight).
Figure 6B:
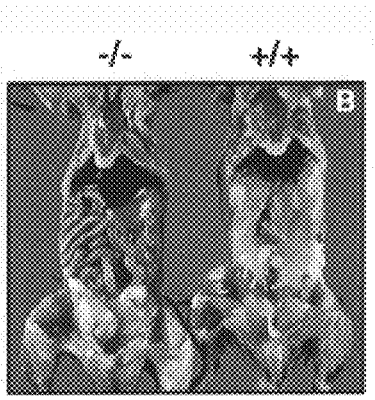
FIG. 6B shows abdominal view of the fat pads under the skin of $Acc2^{-/-}$ (−/−) and wild type mice (+/+).
Figure 6C:
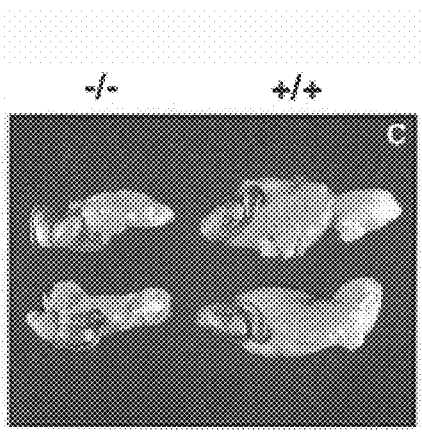
FIG. 6C shows epididymal fat pads isolated from the mutant (−/−, 0.75 g) and wild type (+/+, 1.4 g) mice.

On the average, each ACC2$^{-/-}$ mutant mouse consumed 20–30% more food per week and maintained an average body weight of 21 g; in contrast, each wild-type mouse consumed 202 g of food per week and maintained an average body weight of 23 g. The ACC2$^{-/-}$ mutant mice are generally leaner, weighing about 10% less than the wild-type mice throughout the feeding periods and accumulating less fat in their adipose tissues as seen in FIG. 6. For example, the epididymal fat pad tissue in an Acc2–/– male weighed 0.7 g as compared to 1.5 g in a wild type male littermate. Both aged 32 weeks and fed a normal diet (FIG. 6). These results are noteworthy because they not only confirm the role of ACC2-synthesized malonyl-CoA in the regulation of mitochondrial β-oxidation, they also highlight the importance of mitochondrial oxidation of fatty acids in the regulation of energy homeostasis and in the regulation of fat storage in the adipose tissue.

EXAMPLE 10

Generation of ACC1$^-$ Transgenic Mice

Figure 7A:
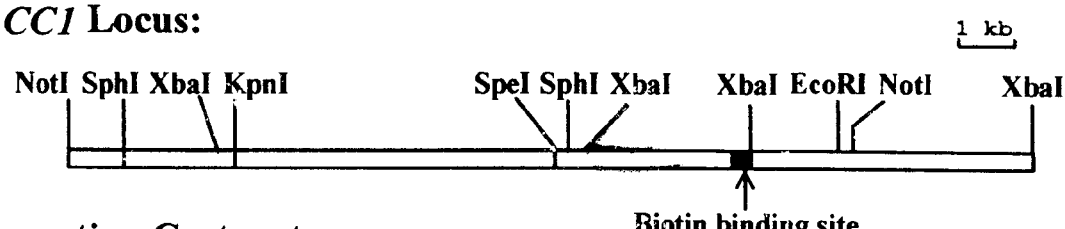
FIGS. 7A and 7B show the targeted mutation of the ACC1 locus.
Figure 7A:
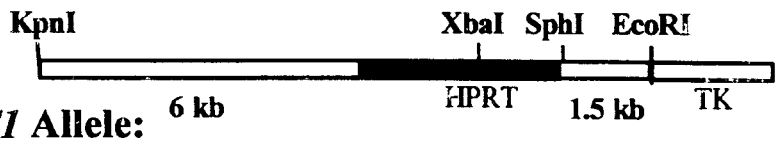
Figure 7A:
Figure 7B:
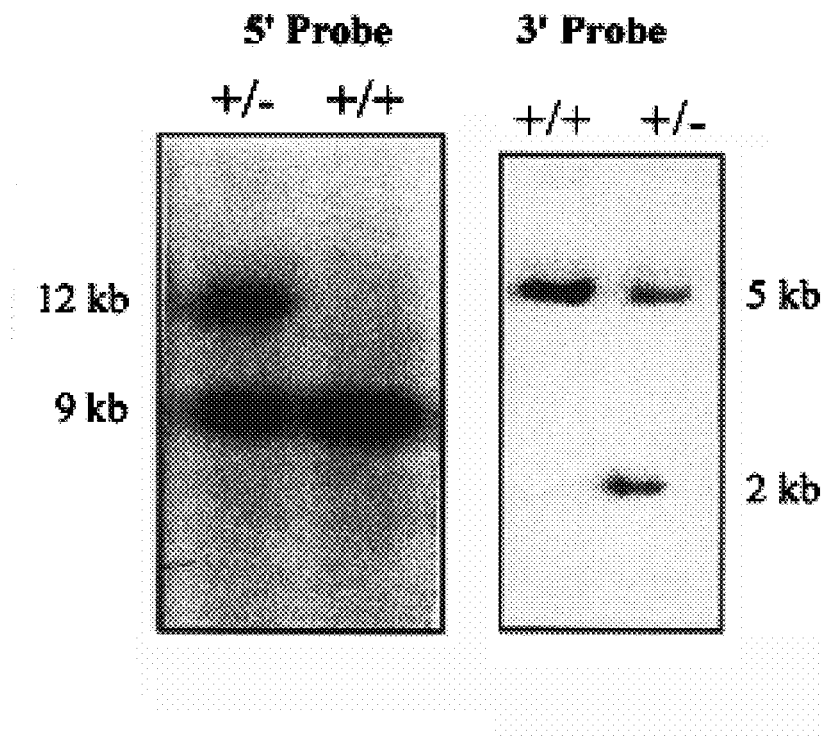

To demonstrate the importance of ACC1 in the de novo synthesis of fatty acids, the same strategy was followed to generate an ACC1-knockout mouse as done for ACC2. Like ACC2, the ACC1 isoform is also highly conserved among animal species (3). A forward primer (5'-GGATATCGCATCACAATTGGC-3') (SEQ ID No. 3) based on the human ACC1 cDNA and a reverse primer (CCTCGGAGTGCCGTGCTCTGGATC-3') (SEQ ID No. 4) that contained the biotin-binding site was designed and used to amplify a 335-bp cDNA probe using human cDNA as a template. A 129/SvEv mouse genomic library was screened with the PCR fragment as described for ACC2, and a 14-kbp clone was isolated, mapped with restriction enzymes, and analyzed by Southern blotting (FIG. 7B). A correctly targeted clone (FIG. 7A) was microinjected into C57BL/6J mouse blastocysts, which were then implanted into the uterine horns of pseudopregnant female mice. The male chimeras thus generated were bred with C57BL/6J mates, and the ACC1 heterozygous offspring were interbred.

After analyzing genomic DNA from more than 300 progenies by Southern blotting using both the 5' and 3' probes, homozygous ACC1-null mutant offspring were not obtained. The litter sizes were less than average, being 6 or 7, and 35% of the progeny were wild-type and 65% were heterozygous. These results demonstrate that the ACC1 mutation is embryonically lethal.

To characterize this embryonic lethality, the mating of the heterozygotes was timed and the resulting embryos were genotyped. At gestation days E12.5 and E13.5, the viable embryos were 35% wild-type and 65% heterozygous, indicating that the lethality had occurred earlier. At gestation day E9.5, the remains of dead embryos were recovered, and at gestation day E8.5, degenerating embryos were recovered from inside the ectoplacental cone.

Discussion

Obesity is a major health factor that affects the body's susceptibility to a variety of diseases such as heart attack, stroke, and diabetes. Obesity is a measure of the fat deposited in the adipose in response to food intake, fatty acid and triglyceride synthesis, fatty acid oxidation, and energy consumption. Excess food provides not only the timely energy needs of the body, but promotes glycogen synthesis and storage in liver and muscle and fatty acid and triglyceride synthesis and storage in the fat tissues. Calorie restriction or starvation promotes glycogenolysis that supplies glucose where needed and lipolysis that supplies fatty acids for oxidation and energy production. Insulin and glucagon are the hormones that coordinate these processes. Malonyl-CoA is the key intermediate in fatty acid synthesis, has recently assumed an additional role as a second messenger that regulates energy levels (ATP) through fatty acid oxidation, which in turn affects fatty acid synthesis and carbohydrate metabolism.

The studies described above provide a definitive characterization of the role of malonyl-CoA produced by ACC2 in the regulation of fatty acid oxidation and energy metabolism. Malonyl-CoA generated by ACC1 is the donor of the $C_2$ units required for fatty acid synthesis. Acetyl CoA, the substrate for ACC1 and ACC2, is the product of pyruvate oxidation, hence studies of the carboxylases interrelate three major metabolic pathways—carbohydrate metabolism, fatty acid synthesis, and fatty acid oxidation.

Studies on animal carboxylases, usually a mixture of ACC1 and ACC2, showed that these enzymes are under long-term control at the transcriptional and translational levels and under short-term regulation by phosphorylation/dephosphorylation of targeted Ser residues and by allosteric modifications by citrate or palmitoyl-CoA (4–6,11,16–24, 29,31). Several kinases have been found to phosphorylate both carboxylases and to reduce their activities. Insulin activates the carboxylases through their dephosphorylation, whereas glucagon and epinephrine inactivate them as a result of their phosphorylation (7–9,20,22,24,25). The AMP-activated protein kinase (AMPK), one of the most notable kinases, is activated by a high level of AMP concurrent to a low level of ATP through mechanisms involving allosteric regulation and phosphorylation by protein kinase (AMPK kinase) in a cascade that is activated by cellular stressors that deplete ATP (10). Through these mechanisms, when metabolic fuel is low and ATP is needed, both the ACC activities are turned off by phosphorylation, resulting in the low malonyl-CoA levels that lead to increased synthesis of ATP through increased fatty acid oxidation and decreased consumption of ATP for fatty acid synthesis.

The differential expression of ACC1 and ACC2 in various tissues—ACC1 is highly expressed in liver and adipose and ACC2 is predominant in heart and muscle—and their cellular localization—ACC1 in the cytosol and ACC2 on the mitochondrial membrane—suggest that their functions are different though interrelated. The cytosolic ACC1-generated malonyl-CoA is utilized by the fatty acid synthase, which also is a cytosolic enzyme, for the synthesis of fatty acids. The mitochondrial ACC2-generated malonyl-CoA functions as a regulator of CPTI activity—CPTI being the first enzyme that catalyzes the shuttling of long-chain fatty acids into the mitochondria for β-oxidation and energy production. ACC2-generated malonyl-CoA, therefore, is a second messenger that regulates ATP levels through fatty acid oxidation, which, in turn, affects fatty acid synthesis and carbohydrate metabolism.

The present studies of the ACC2 mutant mice strongly support this conclusion. The levels of malonyl-CoA in the livers of the mutant mice were similar to those in the livers of the wild-type mice, indicating its synthesis by ACC1, the predominant carboxylase in this tissue. In the livers of the wild-type mice, the malonyl-CoA is used to synthesize fatty acids, which are then converted into triglycerides that accumulate as lipid droplets (FIG. 3A). In the livers of the ACC2$^{-/-}$ mutant mice, the uncontrolled CPTI activity results in the oxidation of fatty acids by the liver mitochondria or in the conversion of fatty acids into lipids (very-low-density lipoproteins), which are then transported through the bloodstream to the heart and muscles to overcome the increased demand of these tissues for fatty acids consequential to uninhibited CPTI activity and amplified fatty acid oxidation. These conclusions were supported by the near absence of malonyl-CoA in the heart and skeletal muscle tissues of the ACC2$^{-/-}$ mutant mice, by the higher fatty acid-oxidation rate in the soleus muscles of the ACC2$^{-/-}$ mutant mice, and by the occurrence of fatty acid oxidation independent of insulin and isoproterenol, an analog of glucagon (FIG. 5).

Finally, knocking out ACC2 in mice has demonstrated that the lack of malonyl-CoA, the mitochondrial second messenger, produces offspring that exhibit increased oxidation of fatty acids, decreased accumulation of lipids, and decreased storage of glycogen in the liver but are still morphologically normal, grow at an expected rate, and breed normally (their longevity and aging are being followed). All of the metabolic changes are expressed in food consumption patterns and body weight—the ACC2$^{-/-}$ mutant mice who were fed a standard diet typically consumed 20% more food than did the wild-type mice yet eventually lost 10% of their body weight. The implications of these results in human development and disease remain to be explored.

The following references were cited herein:

1. Wakil, S. J., Titchener, E. B., and Gibson, D. M., (1958) Biochem. Biopsy. Acta., 29:225-.
2. Wakil, S. J., Stoops, J. K., and Joshi, V. C. (1983) Ann Rev Biochem. 52:537–579.
3. Thampy, K. G. (1989) J Biol Chem. 264:17631–17634.
4. McGarry, J. D., G. P. Mannaerts, and D. W. Foster. (1977) The Journal of Clinical Investigation. 60:265–270.
5. McGarry, J. D., and N. F. Brown. (1997) Eur. J. Biochem. 244:1–14.
6. Abu-Elheiga, L., W. R. Brinkley, L. Zhong, S. S. Chirala, G. Woldegiorgis, and S. Wakil. (2000) Proc Natl Acad Sci USA. 97:1444–1449.
7. Lopaschuk, G., and Gamble, J. (1994) Can J Physiol Pharmacol. 72:1101–1109.
8. Kudo, N., Bar, A. J., R. L., Desai, S., Lopaschuk, G. D. (1995) J Biol Chem. 270:17513–17520.
9. Dyck, J. R., N. Kudo, A. J. Barr, S. P. Davies, D. G. Hardie, and G. D. Lopaschuk. (1999) Eur J Biochem. 262:184–190.
10. Vavvas, D., Apazidis, A., Saha, A. K., Gamble, J., Patel, A., Kemp, B. E., Witters, L. A., and Ruderman, W. B. (1997) J Biol Chem. 272:13255–13261.
11. Alam, N., and E. D. Saggerson. (1998) Biochem J. 334:233–41.
12. Moss, J. and Lane, M. D., (1971) Adv. Enzymology, 35:321-.
13. Abu-Elheiga, L., Jayakumar, A., Baldini, A., Chirala, S. S., and Wakil, S. J. (1995) Proc Natl Acad Sci. USA 92, 4011–4015.
14. Abu-Elheiga, L., Almarza-Ortega, D. B., Baldini, A., and Wakil, S. J. (1997) J Biol Chem. 272, 10669–10677.
15. Ha, J., J. K. Lee, K.-S. Kim, L. A. Witters, and K.-H. Him. (1996) Proc Natl Acad Sci USA. 93:11466–11470.
16. Thampy, K. G., and Wakil, S. J. (1988) J. Biol. Chem. 263, 6447–6453.
17. Bianchi, A., J. L. Evance, A. J. Iverson, A. C. Nordlund, T. D. Watts, and L. A. Witters. (1990) J Biol Chem. 265:1502–1508.
18. McGarry, J. D., and D. W. Foster. (1980) Ann. Rev. Biochem. 49:395–420.
19. Iverson, A. J., A. Bianchi, A. C. Nordlund, and L. A. Witters. (1990) Biochem J. 269:365–371.
20. Kim, K. H., F. Lopez-Casillas, D. H. Bai, X. Luo, and M. E. Pape. (1989) Faseb J. 3:2250–2256.
21. Thampy, K. G., and Wakil, S. J. (1988) J. Biol. Chem. 263, 6454–6458.
22. Mabrouk, G. M., Helmy, I. M., Thampy, K. G., and Wakil, S. J. (1990) J. Biol. Chem. 265, 6330–6338.
23. Mohamed, A. H., W. Y. Huang, W. Huang, K. V. Venkatachalam, and S. J. Wakil. (1994) J Biol Chem. 269:6859–6865.
24. Hardie, D. G. 1989. Prog Lipid Res. 28:117–146.
25. Hardie, D. G., and D. Carling. (1997) Eur J Biochem. 246:259–273.
26. Rasmussen, B. B. and Winder, W. W., (1997), J. Appl. Physiol., 83:1104-.
27. Winder, W. W. and Hardie, D. G., (1996) Am. J. Physiol., 270:E299.
28. Rasmussen, B. B. and Wolfe, R. R., (1999) Ann. Rev. Natr. 19:463-
29. Bressler, R. and Wakil, S. J. (1961) J Biol Chem. 236:1643–1651.
30. Nandendergche, K., E. A. Rishter, and P. Hespel. (1999) Acta Physiol Scand. 165:307–314.
31. Chaudry, I. H., and M. K. Gould. (1969) Biochem Biophys Acta. 177:527–536.
32. Ibrahimi, A. et al., (1999), J. Biol. Chem., 274:26761-.
33. McGarry, J. D., Mills, S. E., Long, C. S., and Foster, D. W., (1983) Biochem. J., 214:21-.
34. Schwartz, M. W., et al. (1996) Diabetes, 45:531-.
35. Zhang, Y., et al., (1994) Nature, 372:425-
36. O'Shea, D. et al. (1997) Endocrinology, 138:196-.
37. Schwartz, M., Erickson, J., Baskin, R., and Palmiter, R. (1998) Endocrinology, 139:2629-.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A transgenic mouse whose genome comprises a homozygous disruption of an endogenous ACC2 gene for the acetyl-CoA carboxylase-2 isoform of acetyl-CoA carboxylase, wherein said disruption inactivates said gene and wherein said mouse does not produce any functional acetyl-CoA carboxylase-2.

2. The mouse of claim 1 wherein one or more exons of said ACC2 gene has been deleted.

3. The mouse of claim 2, wherein said exons have been replaced with heterologous DNA sequences.

4. The mouse of claim 3, wherein said heterologous DNA sequences comprise an HPRT expression cassette.

5. The mouse of claim 4, wherein an exon encoding a biotin binding motif of ACC2 is replaced with an HPRT expression cassette.

6. The mouse of claim 1, wherein said mouse exhibits a phenotype comprising a metabolic reduction in malonyl-CoA production in skeletal muscle and heart.

7. The mouse of claim 6, further comprising a phenotype of unrestricted fat oxidation and reduced fat accumulation in the liver and fat storage cells.

8. The mouse of claim 7, further comprising a phenotype of consuming more calories than a wild type mouse yet accumulating less fat than a wild type mouse.

9. A cell line derived from the transgenic mouse of claim 1.

10. The cell line of claim 9, wherein said cell line is derived from cells selected from the group consisting of muscle cells, heart cells, adipose cells, and liver cells.

* * * * *

UNITED STATES PATENT AND TRADEMARK OFFICE
CERTIFICATE OF CORRECTION

PATENT NO. : 6,548,738 B2
DATED : April 15, 2003
INVENTOR(S) : Salih J. Wakil, Martin M. Matzuk and Lutfi Abu-Elheiga It is certified that error appears in the above-identified patent and that said Letters Patent is hereby corrected as shown below:

Column 1,
Line 65, "Acc2" should read -- ACC2 --.

Column 3,
Lines 39, 65 and 67, "wild type" should be hyphenated.
Lines 51, 54, 56 and 64, "Acc2" should read -- ACC2 --.

Column 4,
Line 1, "Acc2" should read -- ACC2 --.
Line 33, please delete the apostrophe in "DNA's".

Column 5,
Lines 1, 4, 10, 27, 28, 34, 38, 40 and 42, "wild type" should be hyphenated.
Lines 34, 37 and 40, "Acc2" should read -- ACC2 --.

Column 6,
Lines 5 and 9, "wild type" should be hyphenated.
Lines 26, 30, 34, 41 and 47, "Acc2" should read -- ACC2 --.

Column 7,
Line 8, "$Acc2^{tm1\ LAE}$" should read -- $ACC2^{tm1\ LAE}$ --.
Line 24, please change the comma after "$ACC2^{-/-}$" to normal script instead of superscript.
Line 52, "Acc2" should read -- ACC2 --.

Column 8,
Line 33, "wild type" should be hyphenated.

Column 9,
Lines 37, 42, 46, 48 and 53, "Acc2" should read -- ACC2 --.

Column 10,
Line 45, "wild type" should be hyphenated.

Column 11,
Line 13, "Acc2" should read -- ACC2 --.

UNITED STATES PATENT AND TRADEMARK OFFICE
CERTIFICATE OF CORRECTION

PATENT NO. : 6,548,738 B2
DATED : April 15, 2003
INVENTOR(S) : Salih J. Wakil, Martin M. Matzuk and Lutfi Abu-Elheiga It is certified that error appears in the above-identified patent and that said Letters Patent is hereby corrected as shown below:

Column 16,
Lines 57 and 58, "wild type" should be hyphenated.

Signed and Sealed this

Thirteenth Day of April, 2004

JON W. DUDAS
*Acting Director of the United States Patent and Trademark Office*

SEQUENCE LISTING

<160> NUMBER OF SEQ ID NOS: 4

<210> SEQ ID NO 1
<211> LENGTH: 25
<212> TYPE: DNA
<213> ORGANISM: Artificial sequence
<220> FEATURE:
<223> OTHER INFORMATION: Reverse oligonucleotide primer for the PCR
      amplification of the biotin-binding region of ACC2

<400> SEQUENCE: 1
ctgaatgatg gggggctcct gctct                                              25

<210> SEQ ID NO 2
<211> LENGTH: 25
<212> TYPE: DNA
<213> ORGANISM: Artificial sequence
<220> FEATURE:
<223> OTHER INFORMATION: Reverse oligonucleotide primer for the PCR
      amplification of the biotin-binding region of ACC2

<400> SEQUENCE: 2
ttcagccggg tggactttag caagg                                              25

<210> SEQ ID NO 3
<211> LENGTH: 21
<212> TYPE: DNA
<213> ORGANISM: Artificial sequence
<220> FEATURE:
<223> OTHER INFORMATION: Forward oligonucleotide primer for the PCR
      amplification of the biotin-binding region of ACC1

<400> SEQUENCE: 3
ggatatcgca tcacaattgg c                                                  21

<210> SEQ ID NO 4
<211> LENGTH: 24
<212> TYPE: DNA
<213> ORGANISM: Artificial sequence
<220> FEATURE:
<223> OTHER INFORMATION: Reverse oligonucleotide primer for the PCR
      amplification of the biotin-binding region of ACC1

<400> SEQUENCE: 4
cctcggagtg ccgtgctctg gatc                                               24